US008007623B2

(12) United States Patent (10) Patent No.: US 8,007,623 B2
Andrews (45) Date of Patent: Aug. 30, 2011

(54) APPARATUS AND METHOD FOR INTERMITTENT APPLICATION OF STRETCHABLE WEB TO TARGET WEB

(75) Inventor: Robert E Andrews, Sheboygan, WI (US)

(73) Assignee: Curt G. Joa, Inc., Sheboygan Falls, WI (US)

( * ) Notice: Subject to any disclaimer, the term of this patent is extended or adjusted under 35 U.S.C. 154(b) by 0 days.

(21) Appl. No.: 12/383,655

(22) Filed: Mar. 27, 2009

(65) Prior Publication Data

US 2010/0243155 A1 Sep. 30, 2010

(51) Int. Cl.
*B29C 65/00* (2006.01)
*B32B 37/00* (2006.01)
*B32B 38/04* (2006.01)
(52) U.S. Cl. ........ 156/265; 156/519; 156/302; 156/552; 156/557; 156/541; 156/517; 156/285; 156/361
(58) Field of Classification Search .................. 156/519, 156/302, 265, 552, 557, 541, 517, 285, 361
See application file for complete search history.

(56) References Cited

U.S. PATENT DOCUMENTS

| | | | | | |
|---|---|---|---|---|---|
| 3,981,763 | A | * | 9/1976 | Brocklehurst | 156/352 |
| 4,925,520 | A | * | 5/1990 | Beaudoin et al. | 156/494 |
| 5,674,334 | A | * | 10/1997 | Instance | 156/64 |
| 6,766,843 | B2 | * | 7/2004 | Hilt et al. | 156/557 |
| 7,347,914 | B2 | * | 3/2008 | Umebayashi et al. | 156/302 |
| 2006/0266465 | A1 | | 11/2006 | Meyer | |

FOREIGN PATENT DOCUMENTS

| | | |
|---|---|---|
| EP | 1132325 | 9/2001 |
| EP | 1994919 | 11/2008 |
| EP | 2036522 | 3/2009 |

OTHER PUBLICATIONS

European Search Report, 10250536.9-2124, May 20, 2010.

* cited by examiner

*Primary Examiner* — Linda L Gray
(74) *Attorney, Agent, or Firm* — Ryan Kromholz & Manion, S.C.

(57) ABSTRACT

Apparatus and methods are provided to allow for cutting a stretchable first web into segments and securing the segments to a second web. The apparatus includes an infeed rate adjustment apparatus, a tension control device, a cutting apparatus, and means for securing the segments to the second web. The infeed rate adjustment apparatus is sized and configured to adjust the speed of the infeed of the first web to the cutting apparatus to space apart the segments.

18 Claims, 9 Drawing Sheets

APPARATUS AND METHOD FOR INTERMITTENT APPLICATION OF STRETCHABLE WEB TO TARGET WEB

BACKGROUND OF THE INVENTION

The invention disclosed herein relates to apparatus and methods for waste reduction and improvements to the quality and production in web processing operations, such as diaper manufacturing. While the description provided relates to diaper manufacturing, the apparatus and method are easily adaptable to other applications.

Generally, diapers comprise an absorbent insert or patch and a chassis, which, when the diaper is worn, supports the insert proximate a wearer's body. Additionally, diapers may include other various patches, such as tape tab patches, reusable fasteners and the like. The raw materials used in forming a representative insert are typically cellulose pulp, tissue paper, poly, nonwoven web, acquisition, and elastic, although application specific materials are sometimes utilized. Usually, most of the insert raw materials are provided in roll form, and unwound and applied in assembly line fashion.

In the creation of a diaper, multiple roll-fed web processes are typically utilized. To create an absorbent insert, the cellulose pulp is unwound from the provided raw material roll and pulverized by a pulp mill. Discrete pulp cores are formed by a core forming assembly and placed on a continuous tissue web. Optionally, super-absorbent powder may be added to the pulp core. The tissue web is wrapped around the pulp core. The wrapped core is debulked by proceeding through a calender unit, which at least partially compresses the core, thereby increasing its density and structural integrity. After debulking, the tissue-wrapped core is passed through a segregation or knife unit, where individual wrapped cores are cut. The cut cores are conveyed, at the proper pitch, or spacing, to a boundary compression unit.

While the insert cores are being formed, other insert components are being prepared to be presented to the boundary compression unit. For instance, the poly sheet is prepared to receive a cut core. Like the cellulose pulp, poly sheet material is usually provided in roll form. The poly sheet is fed through a splicer and accumulator, coated with an adhesive in a predetermined pattern, and then presented to the boundary compression unit. In addition to the poly sheet, which may form the bottom of the insert, a two-ply top sheet may also be formed in parallel to the core formation. Representative plies are an acquisition web material and a nonwoven web material, both of which are fed from material rolls, through a splicer and accumulator. The plies are coated with adhesive, adhered together, cut to size, and presented to the boundary compression unit. Therefore, at the boundary compression unit, three components are provided for assembly: the poly bottom sheet, the core, and the two-ply top sheet.

A representative boundary compression unit includes a die roller and a platen roller. When all three insert components are provided to the boundary compression unit, the nip of the rollers properly compresses the boundary of the insert. Thus, provided at the output of the boundary compression unit is a string of interconnected diaper inserts. The diaper inserts are then separated by an insert knife assembly and properly oriented. At this point, the completed insert is ready for placement on a diaper chassis.

A representative diaper chassis comprises nonwoven web material and support structure. The diaper support structure is generally elastic and may include leg elastic, waistband elastic and belly band elastic. The support structure is usually sandwiched between layers of the nonwoven web material, which is fed from material rolls, through splicers and accumulators. The chassis may also be provided with several patches, besides the absorbent insert. Representative patches include adhesive tape tabs and resealable closures.

The process utilizes two main carrier webs; a nonwoven web which forms an inner liner web, and an outer web that forms an outwardly facing layer in the finished diaper. In a representative chassis process, the nonwoven web is slit at a slitter station by rotary knives along three lines, thereby forming four webs. One of the lines is on approximately the centerline of the web and the other two lines are parallel to and spaced a short distance from the centerline. The effect of such slicing is twofold; first, to separate the nonwoven web into two inner diaper liners. One liner will become the inside of the front of the diaper, and the second liner will become the inside of the back of that garment. Second, two separate, relatively narrow strips are formed that may be subsequently used to cover and entrap portions of the leg-hole elastics. The strips can be separated physically by an angularly disposed spreader roll and aligned laterally with their downstream target positions on the inner edges of the formed liners.

After the nonwoven web is sliced, an adhesive is applied to the liners in a predetermined pattern in preparation to receive leg-hole elastic. The leg-hole elastic is applied to the liners and then covered with the narrow strips previously separated from the nonwoven web. Adhesive is applied to the outer web, which is then combined with the assembled inner webs having elastic thereon, thereby forming the diaper chassis. Next, after the elastic members have been sandwiched between the inner and outer webs, an adhesive is applied to the chassis. The chassis is now ready to receive an insert.

To assemble the final diaper product, the insert must be combined with the chassis. The placement of the insert onto the chassis occurs on a placement drum or at a patch applicator. The inserts are provided to the chassis on the placement drum at a desired pitch or spacing. The generally flat chassis/insert combination is then folded so that the inner webs face each other, and the combination is trimmed. A sealer bonds the webs at appropriate locations prior to individual diapers being cut from the folded and sealed webs.

The current practice in applying a stretchable web such as a poly web to a second web is involved continuously feeding the poly web into the process which results in poly running full length of product, or alternatively, full length of a constructed insert core which is then placed onto a nonwoven-type chassis. Not all machine configurations can be adapted from a full length poly chassis to a poly insert configuration due to space and/or cost restrictions. It should be understood that application of the poly web along the entire length of the product, rather than only where it is useful, increases the amount of poly material which must be utilized. This is a waste of the material resource and adds additional cost to the product. It is therefore desirable to create a lower cost product by putting poly into the product only where it is useful, instead of the complete product.

However, typical slip/cut application of poly patch to a continuous web doesn't work well because of the elasticity of the poly web. The slip/cut process allows the poly to slip on anvil prior to being cut causing the poly to violently snap back at the moment of cut. This can result in a short patch-long patch output from the slip/cut where one or more of the resulting poly patches are extremely distorted on the carrier web. This result is useless for producing a diaper-type product and would be unacceptable to the consumer. It is therefore desirable to provide an apparatus that can cut patches from a poly web while eliminating the snap back of the poly web material.

SUMMARY OF THE INVENTION

One aspect of the invention is a method including providing a first continuous web of material, the first web being of a stretchable material. The method further includes providing a rotatable anvil having a peripheral surface and a cutting roll positioned to cut segments from a first web against the anvil, the anvil being supplied interiorly with a reduced air pressure and being provided with openings through the peripheral surface, the anvil being sized and configured to continuously rotate at a first velocity. The method further includes feeding the first web toward the anvil at a velocity which is variable between a second velocity and a third velocity. The method further includes intermittently cutting a succession of segments against the peripheral surface of the anvil and conveying each of the segments successively on the rotating peripheral surface, using the reduced air pressure to hold the segments against the peripheral surface. The method further includes providing a second continuous web of material traveling, in close proximity, but displaced from the anvil. The method further includes intermittently applying the successive segments to the second web.

The method may include providing a velocity adjustment apparatus.

The velocity adjustment apparatus of the method may take the form of an infeed conveyor.

The method may include providing a tension control device, which may take the form of a web accumulator.

The method may include securing the segment to the second web.

The intermittently securing step of the method may include applying glue to first continuous web and bringing the second web into contact with the successive segments.

The intermittently securing step of the method may include applying glue to the second continuous web on a surface facing away from the anvil and bringing the second web into contact with the successive segments.

The first stretchable web may take the form of a poly material.

Thee second web of the method may take the form of a composite material for forming disposable diapers.

The cutting roll may take the form of a rotary die.

The infeed conveyor may be operated to stop the infeed of the first web to the anvil for a predetermined amount of time after each successive segment is cut.

Another aspect of the invention is an apparatus including a cylindrical anvil roll with a pattern of vacuum openings on a peripheral surface thereof and means for drawing a vacuum within said cylindrical anvil, means for feeding a continuous web of stretchable material onto said anvil at a rate which is variable between a first velocity and a second velocity, means for controlling the tension in the first web, a knife roll positioned to cut said web of stretchable material against said anvil to create a succession of spaced apart segments, and means for transporting a second web in contact with said anvil.

The means for feeding the continuous web may take the form of an infeed conveyor. The means for controlling the tension may take the form of a web accumulator. The apparatus may include means for securing the spaced apart segments to the second web. The means for securing the segments of the second web may take the form of an adhesive applicator sized and configured to apply adhesive to an engaging surface of the first web.

The means for securing the segments of the second web may take the form of an adhesive applicator sized and configured to apply adhesive to an engaging surface of the second web.

DESCRIPTION OF THE PREFERRED EMBODIMENT

Although the disclosure hereof is detailed and exact to enable those skilled in the art to practice the invention, the physical embodiments herein disclosed merely exemplify the invention which may be embodied in other specific structures. While the preferred embodiment has been described, the details may be changed without departing from the invention, which is defined by the claims.

Figure 5:
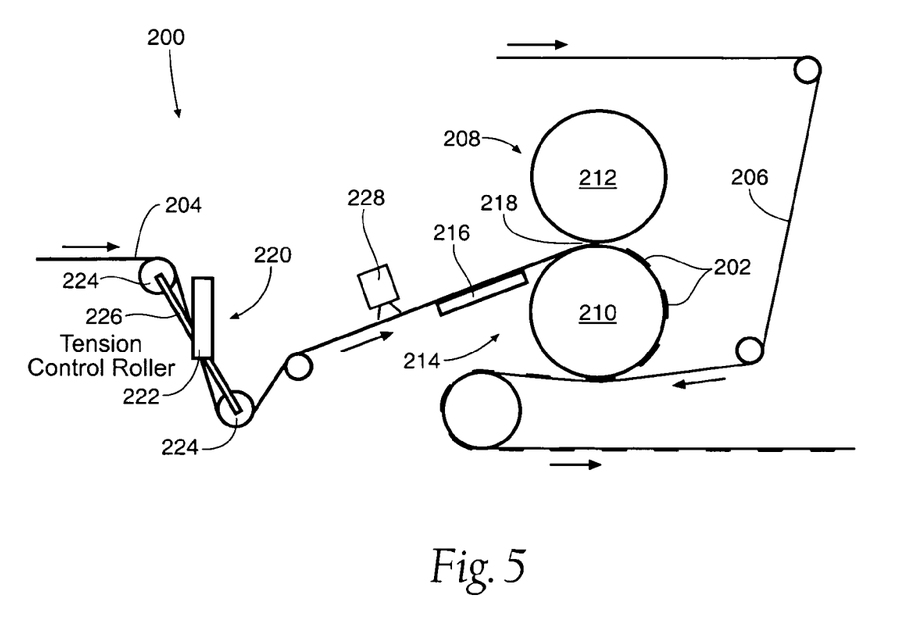
FIG. 5 is a schematic of an embodiment of an apparatus for intermittent application of a stretchable web to a target web.
Figure 6:
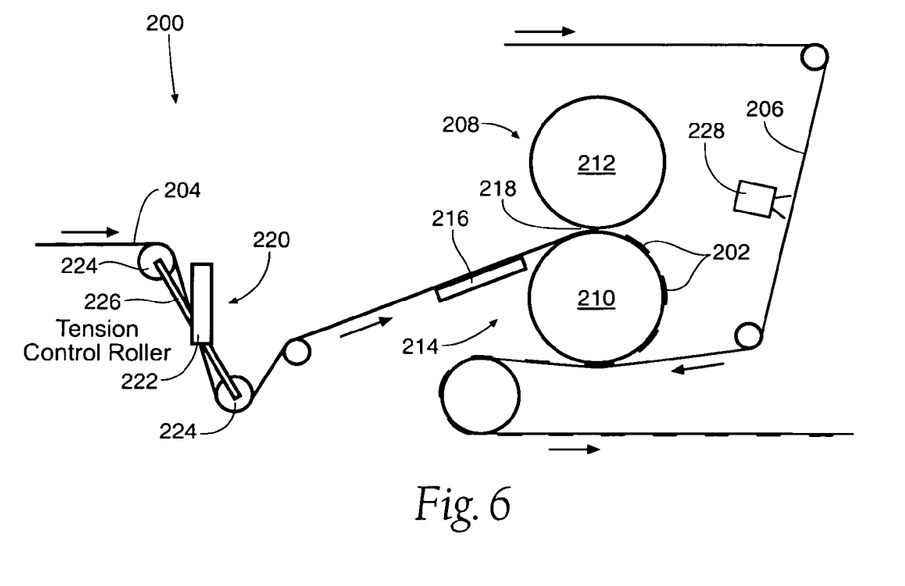
FIG. 6 is an alternative embodiment of an apparatus for intermittent application of a stretchable web to a target web.

It is noted that the present techniques and apparatus are described herein with respect to products such as diapers, but as previously mentioned, can be applied to a wide variety of processes in which discrete components are applied sequentially. FIGS. 1-4 describe diaper making generally and schematically, while FIGS. 5 and 6 show inventive apparatus and techniques for intermittent poly introduction into systems for making products such as diapers.

Figure 1:
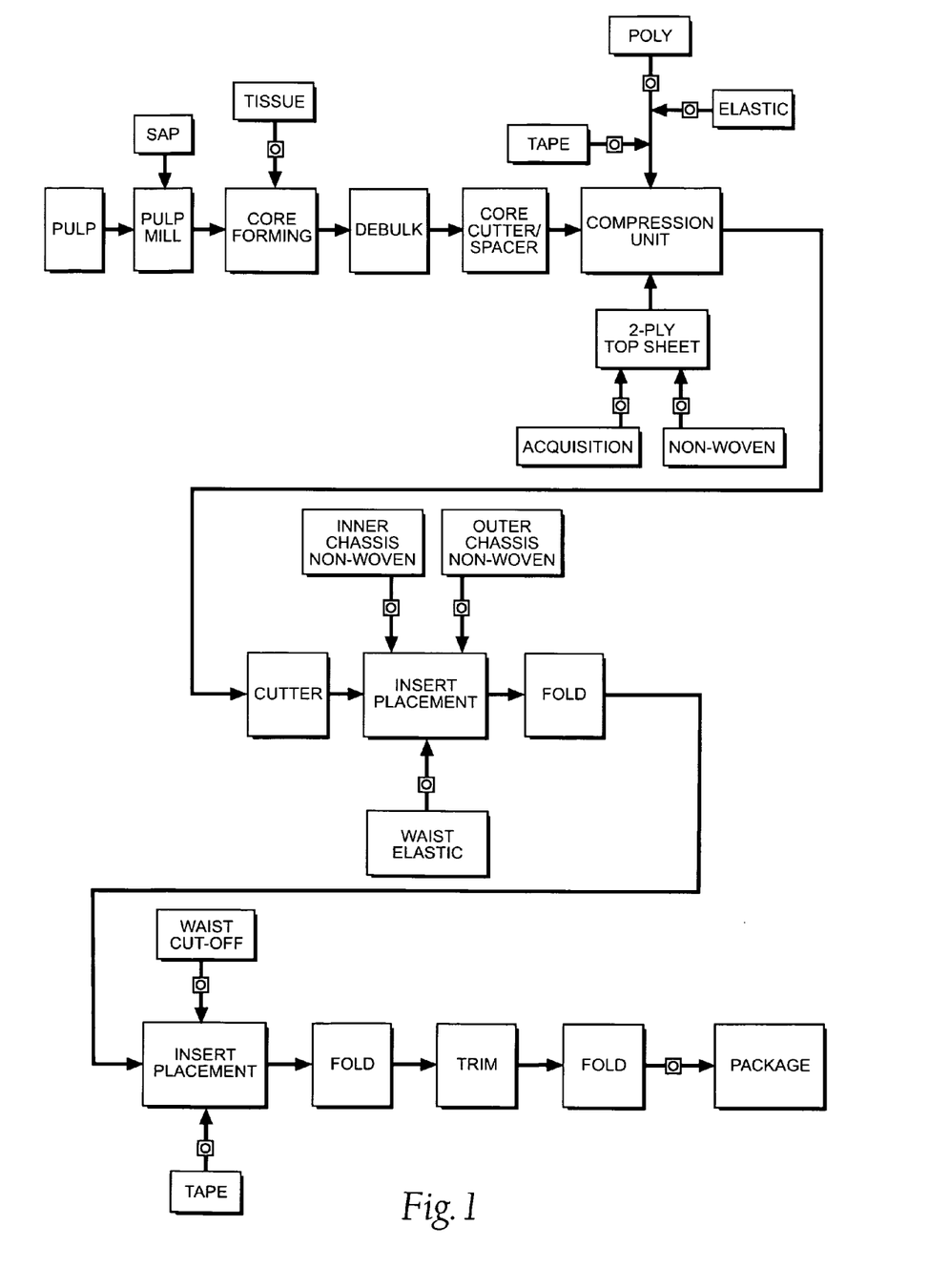
FIG. 1 is a schematic of a representative web processing system.

Referring to FIG. 1, a web processing operation starts with incorporating raw materials such as paper pulp and super absorbent polymer (SAP) in a pulp mill. The mixture is sent to a core forming drum, where cores are formed for retaining liquids. A core can be placed on a tissue and processed as shown. Eventually, an additional tissue layer is formed, sandwiching the core.

The process continues through debulking, core cutting and spacing, optionally, compression, and application of tape and elastics. The process then proceeds with application of outer and inner non-woven layers, and waist elastic. The web can undergo folding, extraction and trimming of excess material, and application of material to tighten the diaper about the waist. Eventually, the product is folded and packaged.

As seen on FIG. 1, the symbol is shown at locations of introductions of discrete components into the process. At these locations, inspection can take place to determine the presence or absence of acceptable product introduction. In addition to visual inspection, operational characteristics such as startup/ramp-up/shutdown operations can trigger waste minimization techniques as will be described later.

At each of these operations shown in FIG. 1, diagnostics can be performed to indicate whether the product meets acceptable criteria. If so, discrete elements, such as the core, tissue layers, elastic, etc., continue to be applied in a sequence such as shown in FIG. 1. If not, no additional discrete elements need be applied.

Figure 2A:
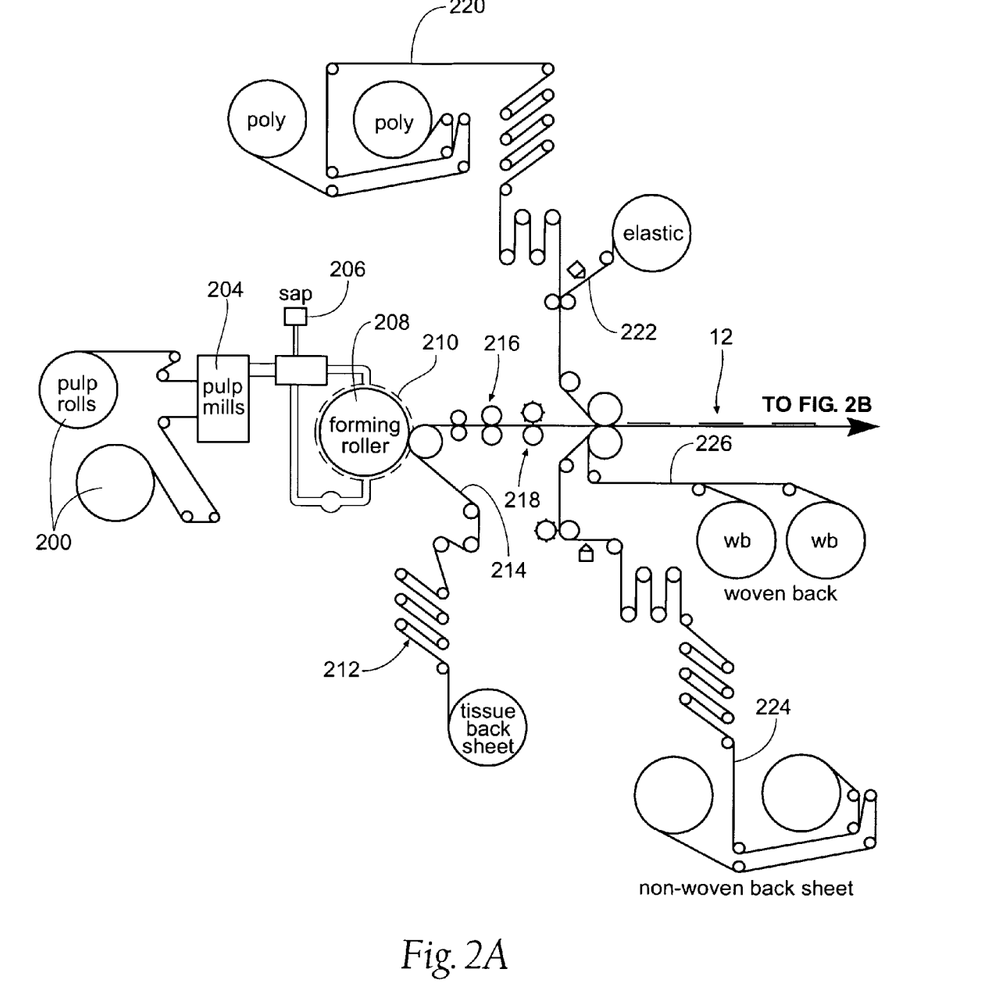
FIGS. 2A-2C are schematic representations of a web processing system incorporating principles of the present invention.
Figure 2B:
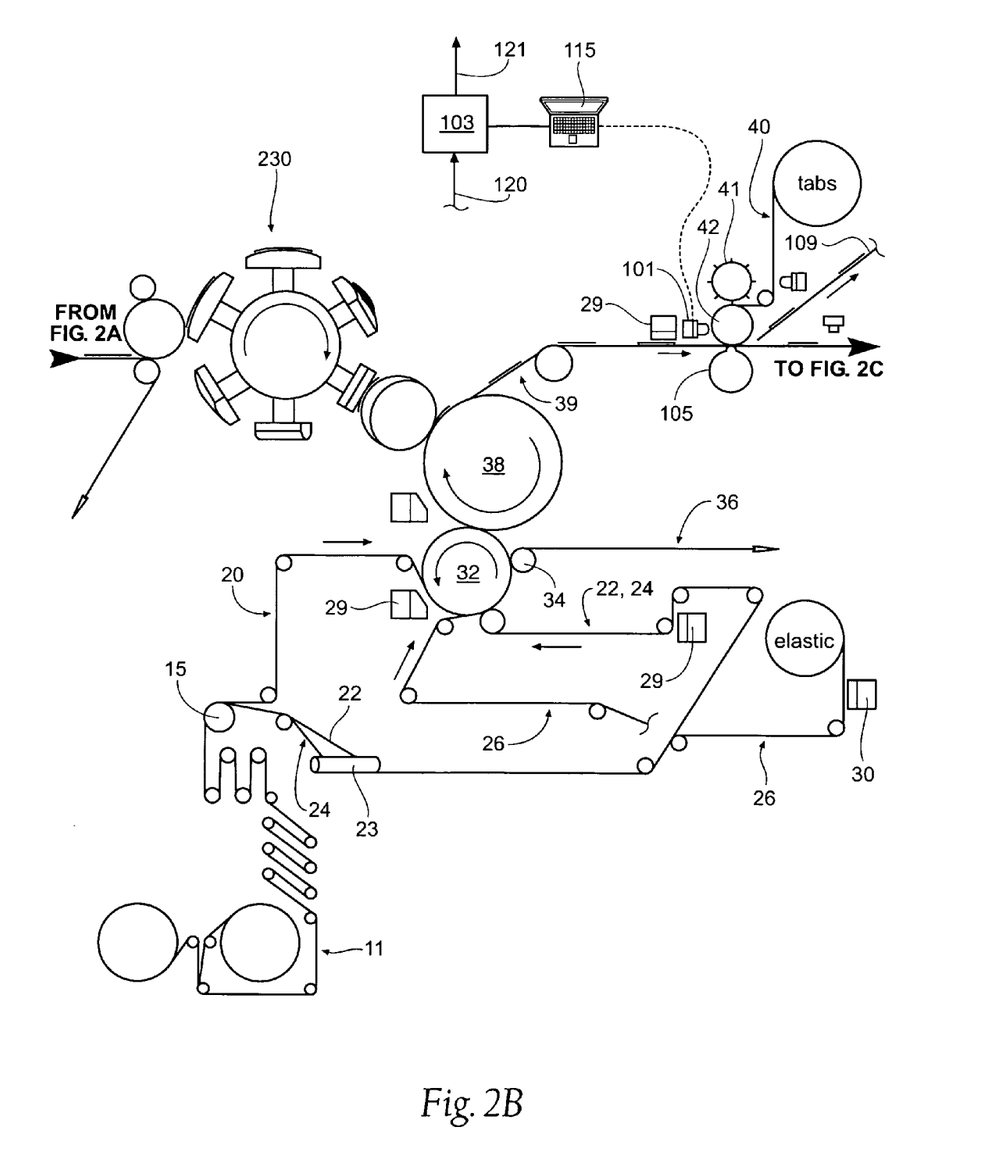
Figure 2C:
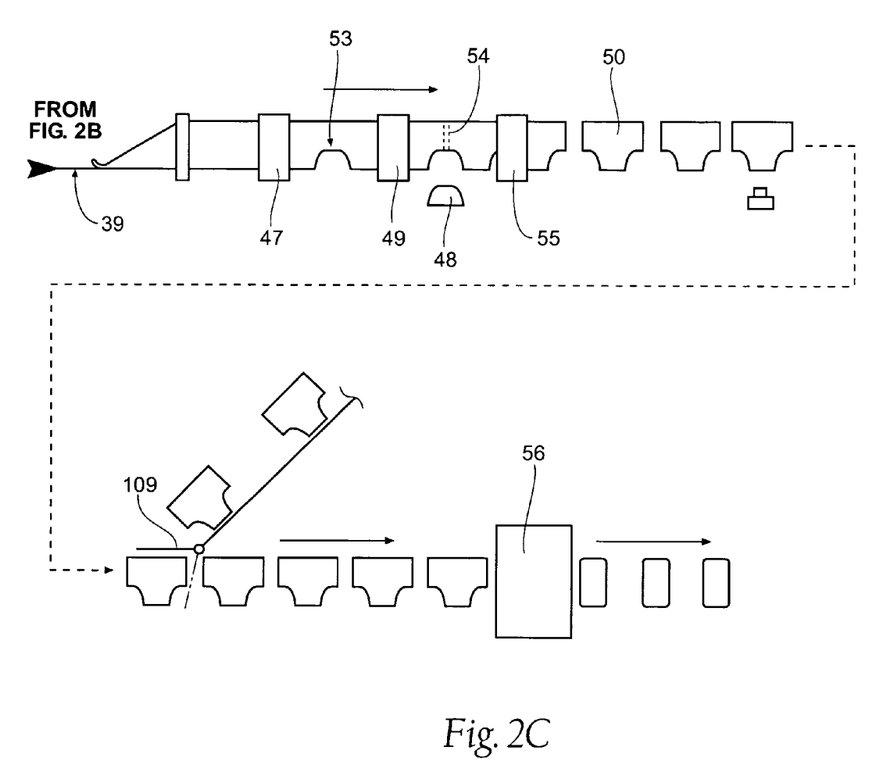
Figure 3:
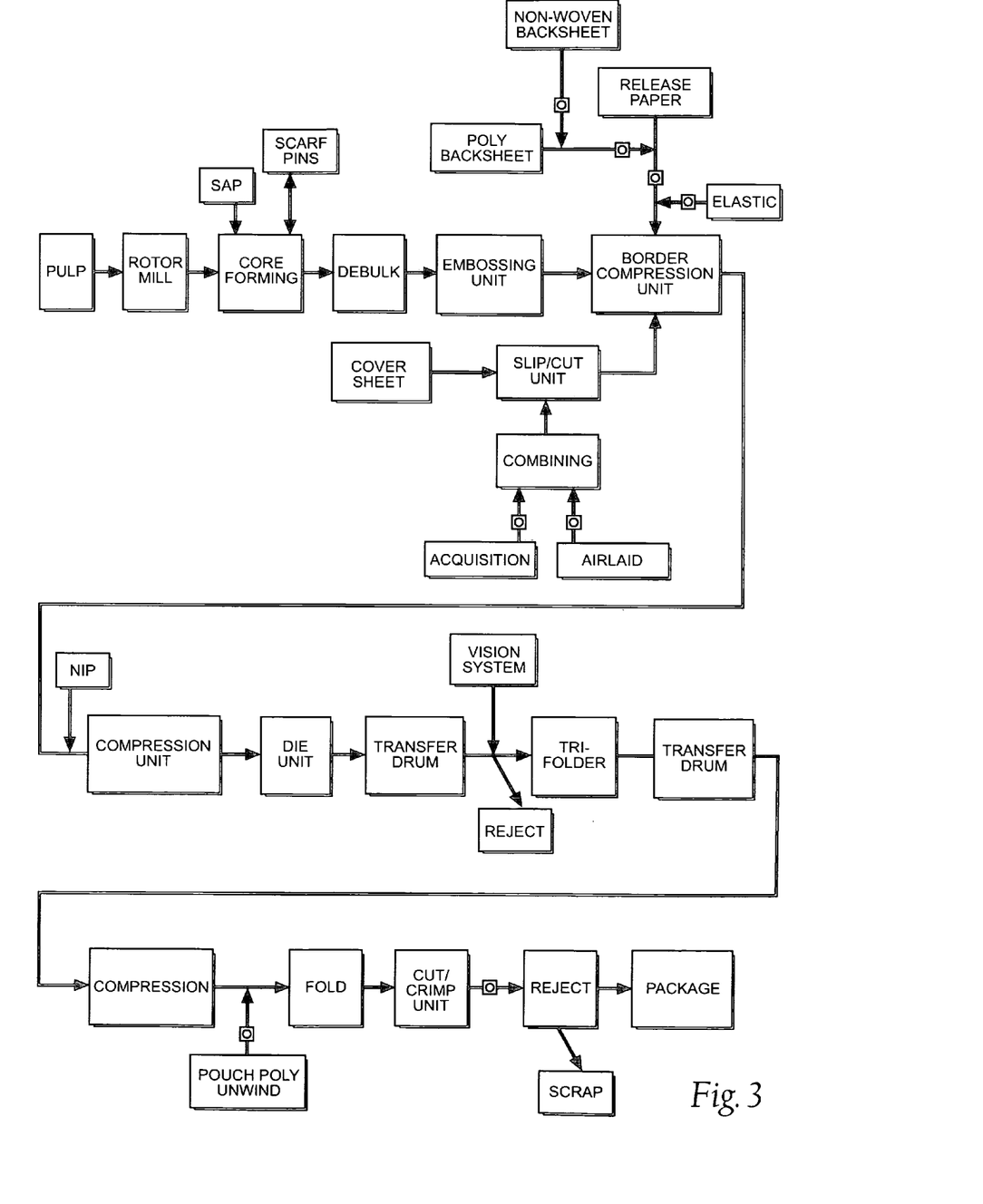
FIG. 3 is a schematic of a second embodiment of a representative web processing system.
Figure 4A:
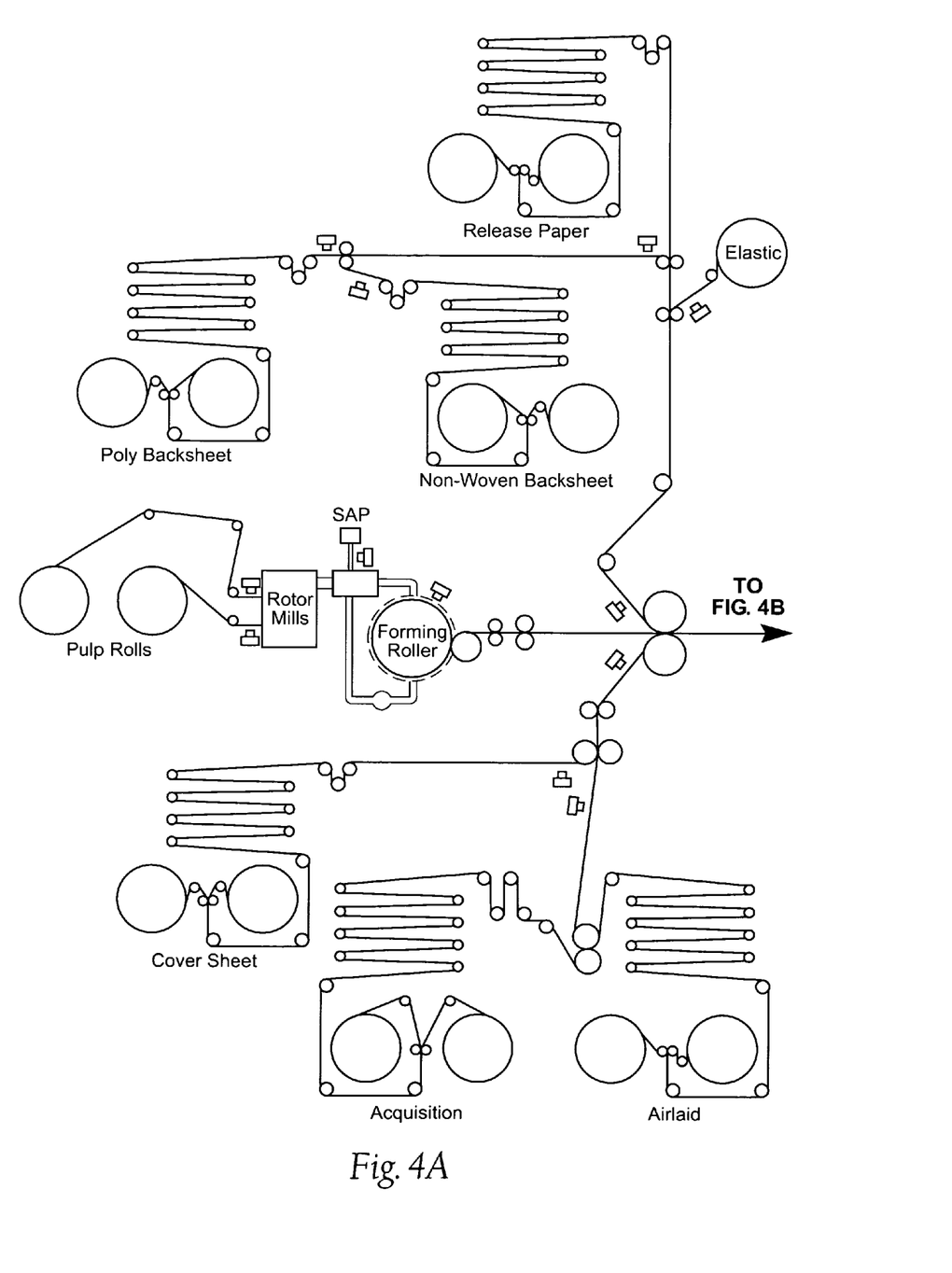
FIGS. 4A-4C are additional schematic representations of a web processing system.
Figure 4B:
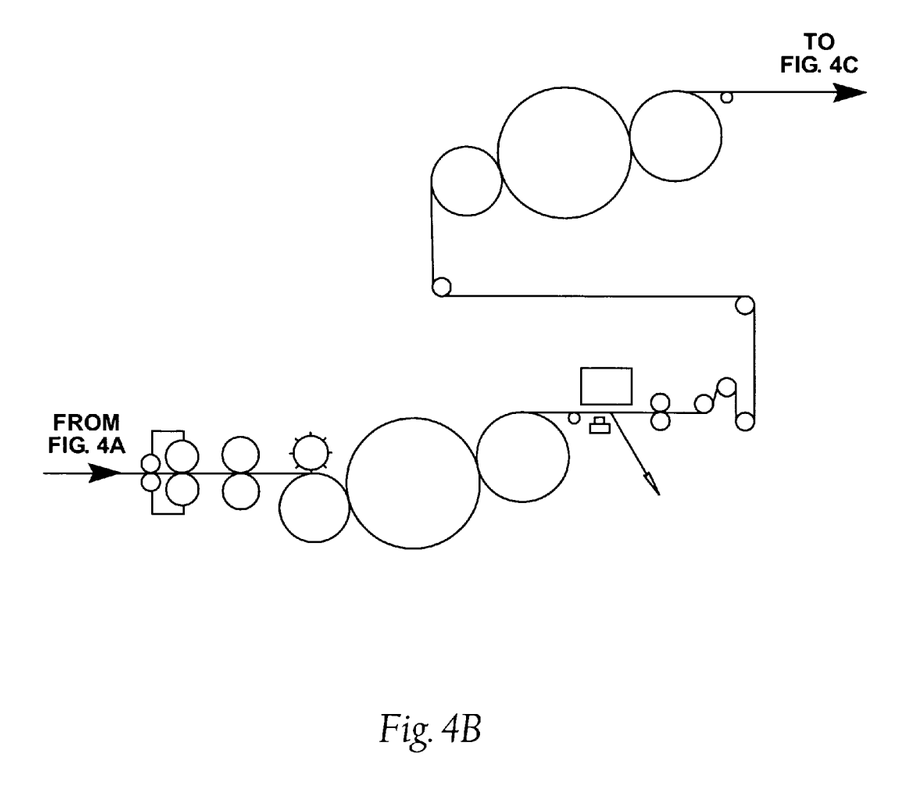
Figure 4C:
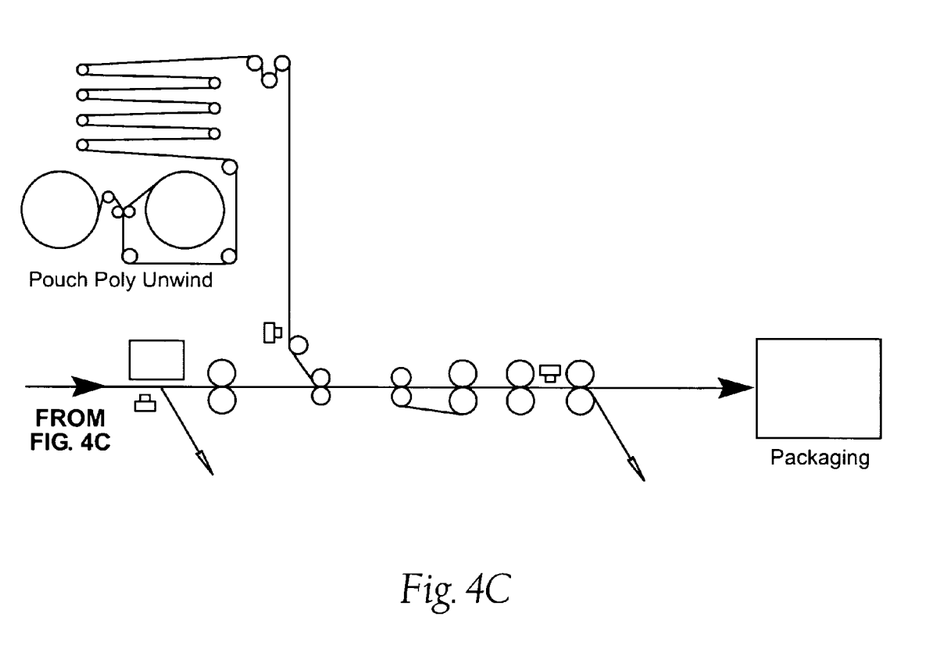

Referring now to FIGS. 2*a-c*, a web processing operation incorporating the present invention is shown.

Referring now to FIG. 2, an additional schematic of processes of diaper making processes are shown. As indicated, pulp rolls 200 feed raw pulp 201 into a pulp mill 204, where the pulp is pulverized. Super absorbent polymer is added from station 206. The SAP laced pulp is fed onto core forming roller 208. Cores 210 from the core forming roller 208 are applied to the tissue back sheet 214 which has been introduced through tissue back sheet feeder 212. Following debulking station 216 and the core cutting and spacing station 218, an infeed of poly layer 220, elastic layer 222 is applied to the carrier web, in addition to a non woven layer 224 and two ply top sheet woven 226. This web then is cut at a cutting station 228 into discrete inserts 230, which are then placed on an article transfer and placement apparatus with active puck 230 such as is disclosed in U.S. patent application Ser. No. 11/357,546, owned by the same assignee as the present case, and which is incorporated herein by reference.

The process utilizes two main carrier webs; a nonwoven web 11 which forms an inner liner web, and a web 12 that forms an outwardly facing layer in the finished diaper 50. In an exemplary embodiment, the nonwoven web 11 is slit, at a slitter station 15, by rotary knives 14 along three lines. One of these lines is preferably on approximately the centerline of a web 11 and the other two lines are parallel to and spaced a short distance from the centerline. The effect is twofold; first, to separate the web 11 into two inner liners 20. One liner will become the inside of the front of the diaper 50 and the second liner will become the inside of the back of that garment. Second, two separate, relatively narrow strips 22 and 24 are formed which are subsequently used to cover and entrap portions of leg-hole elastics 26. Strips 22 and 24 are separated physically by an angularly disposed spreader roll 23 and aligned laterally with their downstream target positions on the inner edges of the liner webs 20.

Adhesive patterns are applied to the liner webs 20 in target areas for the leg-hole elastics 26. A spray gun assembly 29 of a type known in the art is preferably used to apply the adhesive patterns. Two sets of leg-hole, elastic strands 26 are introduced through laydown guides 30, which reciprocate from side to side past each other. The strands 26 are glued to the web sections 20, their laydown patterns following a serpentine path. Given the absence of adhesive in the area separating the inner liners 20, for some portion of each successive diaper product, the strands 26 each track parallel to the inner slit edges of the web sections 20. Laydown guides 30 then apply the strands 26, which form leg-hole elastics as the web sections 20 are carried along the face of a drum or roll 32. Those parts of the elastic patterns which are near the inner slit edges of webs 20 are then covered by the introduction of an adhesive lamination thereover of the strips 22 and 24 of nonwoven web also against the drum 32.

The side-to-side excursions of the leg-hole elastic laydown guides 30 result in arcuate segments of elastic strands extending on each side of the web centerline. After the nonwoven strips 22 and 24 have been applied to cover and entrap those parts of the elastics 26 that run nearest to and parallel to the inner edges of the webs 20, a second pair of slitter knives 34 is used to trim away a portion of the narrow nonwoven strips 22, 24, along with that part of the inner liner webs 20 to which they are laminated. This also removes those portions of the elastic strands 26 which are contained within the laminations. The resultant trimmed scrap strips 36 are removed from the process for disposal elsewhere.

The effect of the last-described step is to remove the cut away portions of the elastic, eliminating its corresponding unwanted gathering effect from the crotch region of the garments 50. The remaining portions of the curved elastic strands create a gathering effect around the leg openings of the finished garments 50.

Subsequent to the combining and trimming of the inner webs 20 and the cover strips 22, 24, the combining drum 32 carries the webs to a nip with a second combining drum 38, where the web sections 20, with their respective curved elastic patterns exposed, are transferred to and laminated adhesively against the inside face of outer liner web 12. This process entraps the curved elastic patterns 26 between the inner liners 20 and outer web 12 thereby forming a composite web 39.

The composite web 39 is then provided with a pattern of adhesive in preparation to receive an absorbent insert or patch 46. The patch 46 is cut from a provided patch web 40 by a cooperation of a cutter 41 and an anvil surface on a vacuum roll 42 and rotated into position for transfer to the composite web 39 by a patch applicator 105. If the patch 46 is to be applied to the web 39—a determination explained more fully below-the patch applicator 105 forces the web 39 against the patch 46, thereby adhering the patch 46 to the web 39.

Leg-hole materials 48, if not previously removed, are cut at a cutting station 47, thereby removing the material 48 contained within an approximate perimeter defined by the curved pattern of the elastics 26. The running composite chassis web 39 is folded, before or after cutting out of the leg holes, longitudinally along its centerline, thereby generally aligning its front waist edge with its back waist edge. The regions 53 which are to become the side seams 54 of the garments 50 are then welded by a sealing device 49 either ultrasonically or by heat. Note that the leg holes are preferably cut out before this point, leaving only a narrow zone for welding. The weld pattern is preferably wide enough to extend into both the left side seam of one garment and the right side seam of the adjacent garment. The garments 50 are then separated by passing through a cut-off knife assembly 55, which severs the web along the transverse axis of the side seam weld 53. The garments 50 can then undergo visual inspection/rejection, and folding, stacking, and packaging as desired at folder/stacker/packager 56.

In addition to the exemplary components generally found in a web processing apparatus, the present device and methods further include an advanced defect detection system. An embodiment of the defect detection system preferably comprises at least one visual inspection station 101, but preferably a plurality of visual inspection stations 101. Each visual inspection station 101 may include a vision sensor, such as an In-Sight Vision Sensor available from Cognex Corporation of Natick, Mass. Since each component part of a product resulting from a web process has a point of incorporation into the product, visual inspection of each component part preferably occurs prior to the point of incorporation. The results of the visual inspections that occur are relayed from each visual inspection station 101 to a programmable logic controller (PLC) 103. Each visual inspection station 101 may provide diagnostic capability by monitoring lighting, focus and positioning.

Machine vision systems typically require digital input/output devices and computer networks to control other manufacturing equipment, in this case the splicing unit.

A typical machine vision system will consist of several among the following components:

One or more digital or analog camera (black-and-white or color) with suitable optics for acquiring images Lighting Camera interface for digitizing images (widely known as a "frame grabber")

A processor (often a PC or embedded processor, such as a DSP)

Computer software to process images and detect relevant features.

A synchronizing sensor for part detection (often an optical or magnetic sensor) to trigger image acquisition and processing.

Input/Output hardware (e.g. digital I/O) or communication links (e.g. network connection or RS-232) to report results Some form of actuators used to sort or reject defective parts.

The sync sensor determines when a part (often moving on a conveyor) is in position to be inspected. The sensor triggers the camera to take a picture of the part as it passes by the camera and often synchronizes a lighting pulse. The lighting used to illuminate the part is designed to highlight features of interest and obscure or minimize the appearance of features that are not of interest (such as shadows or reflections).

The camera's image can be captured by the framegrabber. A framegrabber is a digitizing device (within a smart camera or as a separate computer card) that converts the output of the camera to digital format (typically a two dimensional array of numbers, corresponding to the luminous intensity level of the corresponding point in the field of view, called pixel) and places the image in computer memory so that it may be processed by the machine vision software.

The software will typically take several steps to process an image. In this case, the image processing will result in either detection of the indicator material, or non-detection of the indicator material.

Commercial and open source machine vision software packages typically include a number of different image processing techniques such as the following:

Pixel counting: counts the number of light or dark pixels

Thresholding: converts an image with gray tones to simply black and white

Segmentation: used to locate and/or count parts

Blob discovery & manipulation: inspecting an image for discrete blobs of connected pixels (e.g. a black hole in a grey object) as image landmarks. These blobs frequently represent optical targets for machining, robotic capture, or manufacturing failure.

Recognition-by-components: extracting geons from visual input

Robust pattern recognition: location of an object that may be rotated, partially hidden by another object, or varying in size Barcode reading: decoding of 1D and 2D codes designed to be read or scanned by machines Optical character recognition: automated reading of text such as serial numbers Gauging: measurement of object dimensions in inches or millimeters Edge detection: finding object edges Template matching: finding, matching, and/or counting specific patterns.

In most cases, a machine vision system will use a sequential combination of these processing techniques to perform a complete inspection. A system that reads a barcode may also check a surface for scratches or tampering and measure the length and width of a machined component.

Additionally, machine downtime can be minimized by the provision of systems and methods for warning a machine operator of expected machine troubles so that scheduled maintenance can occur.

The PLC 103 includes software adapted to run several routines that may be initiated by some triggering event, such as an automatic detection of a defined condition or manual input by a machine operator. Some routines are run during machine setup while other routines are run during machine operation, while still other routines are run during machine diagnostics at some point during machine downtime.

The PLC 103 generally receives inputs 120 from the visual inspection stations 101, from the various machine components, or from manual input by a machine operator on an operator interface, or human machine interface (HMI) 115. Some of the inputs can also be from stations near the pulp rolls, pulp mills, forming rollers, or elsewhere in the system where inspection is present.

The HMI 115 provides an interface for user interaction with the web processing machinery and may comprise a pressure sensitive touch screen, a keyboard, a computer mouse, or even a wireless device providing such an interface. The PLC 103 preferably provides controlling outputs 121 to the patch applicator 105, the cutter 41 and vacuum roll 42, a patch reject conveyor 107 and a product reject conveyor 109.

The input to the PLC 103 from each inspection station 101 preferably comprises a defect indicator 111 that represents a detected web defect at a position in the process a number of patch placements from the patch applicator 105. That is, at any given time during machine operation, between any inspection station 101 and any patch applicator 105 in a web process, there exists material sufficient to produce a determinable number of products having a patch applied thereto. Therefore, a defect may be detected and flagged as corresponding to a specific product location throughout the process.

In determining whether a patch should be applied to a product by a patch applicator 105, the PLC 103 stores a product status indicator for each product in the process, preferably for each product between the product reject conveyor 109 and most remote visual inspection station 101. The status indicator accumulates defect indicators 111 from the inspection stations 101 to track the progress of a product through the process.

A preferred product status indicator is a byte of digital data, with each bit reflecting the defect indicator 111 for the tagged product from an inspection station 101. For example, the least significant bit in the status indicator may represent the defect indicator for the most remote visual inspection station 101. As the bit significance increases, so does the proximity of the respective inspection station 101 to the product reject conveyor 109. A byte of data would provide for the possibility of eight inspection stations, and specific tracking of defects at those inspection stations. To store the product status indicator, the PLC 103 preferably includes some volatile and some nonvolatile computer memory. The volatile memory may provide quicker access times during machine operation, while the nonvolatile memory could be used to store product status indicators when the machine is paused. The minimum amount of memory required by the PLC 103 is at least partly determined by the number of visual inspection stations 101 and the number of potential products in queue between the first visual inspection station 101 and the product reject conveyor 109. For example, if a web process utilizes eight visual inspection stations 101 and two hundred products could be in queue in any given time, a volatile memory of at least two hundred bytes would be required.

The visual inspection station outputs may be sampled synchronously, or the outputs may be asynchronously analyzed by the PLC 103. If synchronous, the outputs may be sampled at a rate equal to the speed of the traveling webs divided by the product pitch, or product size. To enable use of different product sizes in a given process, the sample timing of the inspection station results may be varied, accordingly.

In addition to synchronous sampling of the inspection station results, the results could be analyzed asynchronously, which may be advantageous if various materials are incorporated into the process at different rates. Asynchronous analysis of the outputs, however, may provide less visibility into the specific defects included in a completed product.

Referring now to FIGS. 3 and 4a-c, an additional embodiment of a representative web processing system is shown schematically and incorporating principles of the present invention. It is noted that throughout the web processing, inspection systems can be incorporated virtually anywhere, particularly at locations of raw material input into the process.

Referring now to FIG. 5, a diagrammatic view of a system 200 for intermittently applying segments 202 of a stretchable material to a target web 206 is shown. The intermittent poly application apparatus and method can be employed at locations of desired poly introduction into the systems of FIGS. 1, 2a-2c, FIG. 3, or FIGS. 4a-c. The intermittent poly application apparatus and method can also be used on other, non-poly application processes where intermittent application of a certain component is desired.

As shown in FIG. 5 the apparatus 200 preferably includes a first continuous web 204 of stretchable material. The stretchable material may be of any type known in the art including, but not limited to a poly material. The system 200 further includes a second continuous web 206. The second continuous web 206 is preferably of a nonwoven material. The first continuous web 204 is cut into segments 202 and applied to the second continuous web 206.

The system 200 preferably includes a cutting apparatus 208 for cutting the first continuous web 204 into segments 202. The cutting apparatus may take any form known in the art.

Accumulator 220 can take any form, such as a servo driven roller that speeds up and slows down, an alternate roller configuration, a rocking roller configuration such as shown in FIG. 5, or any different means of accumulating the web, such as a miniature accumulator, or a device similar to a diaper cross-folder, or a tucker blade. A similar blade with low inertia could also be employed.

In the illustrated embodiment the cutting apparatus 208 includes an anvil 210 and a knife roll 212. The anvil 210 is preferably a vacuum anvil. As shown in FIG. 5, the first web 204 of material fed against the anvil 210 surface and is cut into segments 202 by the. knife roll 212.

The system 200 preferably includes a rate adjustment apparatus 214. The rate adjustment apparatus 214 is sized and configured to adjust the rate at which the first web 204 is being fed to the anvil 210 while the rate at which the first web 204 is fed to the rate adjustment apparatus 214 remains the same. In the illustrated embodiment, the rate adjustment apparatus 214 takes the form of an infeed conveyor 216 which controls the feed rate of the first web 204 to the anvil 210.

Preferably, after each segment 202 is cut, the infeed of first web 204 to the anvil 210 is momentarily halted. After an appropriate amount of time has passed, the infeed of the first web 204 to the anvil 210 is resumed. In this manner, the segments 202 may be spaced apart when placed on the second web 206. It is contemplated that the leading edge 218 of the first web 204 will engage at least a portion of the vacuum anvil 210 after each segment 202 is cut. Preferably, the vacuum anvil 210 is provided with a relatively low amount of vacuum at that point. The vacuum is preferably sufficient to retain the leading edge 218 of the first web 204 in position, with the anvil 210 slipping below the first web 204. However, the vacuum must be low enough that it does not stretch the first web 204. It should be understood that this may achieved using any means known in the art including, but not limited to a vacuum manifold.

In a preferred embodiment, after the cut is performed at anvil 210, the supply of incoming web 204 to the anvil 218 is momentarily stalled, which results in a gap between supply of the discrete pieces of material 202 to the web 206. Preferably next, the incoming web 204 is then accelerated to feed material to match or nearly match the velocity of roll 210 until the next cut is made. In this sense, the accumulator 220 is used to create the intermittency. The purpose of the speeding and stalling is to prevent snap back of the incoming web 204.

It is further contemplated that the system 200 may include a tension control device 220. The tension control device 220 is preferably sized and configured to eliminate tension in the first web 204 prior to cutting a segment 202 from the first web 204. In this manner when the cut is made the material will not snap back as it would if the first web 204 were under tension. In the illustrated embodiment the tension control device 220 takes the form of a web accumulator 222. However, it is contemplated that the tension control device 220 could take any form known in the art capable of performing such a function. The tension control device 220 of the illustrated embodiment includes a pair of rollers 224 coupled to a pivoting member 226. The pivoting member 226 is pivotable between a first and second position. In this manner, the first web 204 is accumulated in the tension control device 220 when the rate adjustment apparatus 214 momentarily halts the infeed of the web 204 to the anvil 210 as described above.

It is contemplated that the segments 202 may be secured to the target web 206 in any manner known in the art. For example, and not by way of limitation, an adhesive may be applied to the surface of the first web 204 prior to cutting the poly web into segments as shown in FIG. 5. In such an embodiment the system preferably includes an adhesive applicator 228 configured to apply adhesive to the outer surface of the first web 204. The adhesive applicator 228 may be of any type known in the art.

Alternatively, it is contemplated that adhesive may be applied to the surface of the second web 206 prior to placing the cut segments 202 on the second web 206 as shown in FIG. 6. In such an embodiment the system preferably includes an adhesive applicator 228 configured to apply adhesive to the outer surface of the second web 206. The adhesive applicator 228 may be of any type known in the art.

It is further contemplated that the web segments 202 may be ultrasonically bonded to the second web 206. Bonding positions could be located at positions similar to glue head 228, but also could be repositioned in the system, or could for instance employ roll 210 as an anvil, and equipped with an additional roll to react with roll 210, for instance at the 6 o'clock position of roll 210 (not shown in Figs.) Ultrasonic or heat bonding stations could also be employed.

It is contemplated that the system 200 will provide active tension control and feed approach to change the feed of the first web 204 into the slip/cut cutting apparatus 208 at the moment of cut so the first web 204 is not under tension at the cut moment. This will result in a stable cut segment 202 that can be uniformly applied to the second web 206.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

I claim:

1. A method for intermittently applying segments of a first web of material onto a second web of material comprising:
   providing a first continuous web of material, the first web being of a stretchable material;
   providing a rotatable anvil having a peripheral surface and a cutting roll positioned to cut segments from the first web against said anvil, said anvil being supplied interiorly with a reduced air pressure and being provided with openings through said peripheral surface, said anvil being sized and configured to continuously rotate at a first velocity;
   feeding said first web toward said anvil at an infeed velocity; and
   varying said infeed velocity between a first infeed velocity and a second infeed velocity while said web is being fed toward said anvil;
   intermittently cutting a succession of segments against said peripheral surface of said anvil while said infeed velocity is at said first infeed velocity and conveying each of said segments successively on said rotating peripheral surface, using said reduced air pressure to hold said segments against said peripheral surface, and then varying said infeed velocity to said second infeed velocity;
   providing a second continuous web of material traveling, in close proximity, but displaced from said anvil;
   intermittently applying the successive segments to the second web.

2. The method of claim 1 further comprising providing a velocity adjustment apparatus.

3. The method of claim 2 wherein the velocity adjustment apparatus takes the form of an infeed conveyor.

4. The method of claim 3 further comprising
   providing a tension control device.

5. The method of claim 4 wherein the tension control device takes the form of a web accumulator.

6. The method of claim 5 further comprising securing the segments to the second web.

7. The method of claim 6 wherein the intermittently securing step further comprises
   applying glue to first continuous web; and
   bringing the second web into contact with the successive segments.

8. The method of claim 6 wherein the securing step further comprises
   applying glue to the second continuous web on a surface facing away from the anvil; and
   bringing the second web into contact with the successive segments.

9. The method of claim 8 wherein the first stretchable web comprises a poly material.

10. The method of claim 9 wherein the second web comprises a composite material for forming disposable diapers.

11. The method of claim 10 wherein the cutting roll comprises a rotary die.

12. The method of claim 6 wherein the infeed conveyor is operated to stop the infeed of the first web to the anvil for a predetermined amount of time after each successive segment is cut.

13. An apparatus comprising:
    a cylindrical anvil roll with a pattern of vacuum openings on a peripheral surface thereof and means for drawing a vacuum within said cylindrical anvil;
    means for feeding a continuous web of stretchable material onto said anvil at a variable rate, said rate variable between a first velocity and a second velocity;
    means for controlling the tension in the first web;
    a knife roll, the knife roll positioned to cut said web of stretchable material against said anvil to create a succession of spaced apart segments;
    means for transporting a second web in contact with said anvil.

14. The apparatus of claim 13 wherein means for feeding a continuous web comprises an infeed conveyor.

15. The apparatus of claim 13 wherein means for controlling the tension comprises a web accumulator.

16. The apparatus of claim 13 further comprising means for securing the spaced apart segments to the second web.

17. The apparatus of claim 16 wherein said means for securing the segments to the second web further comprises an adhesive applicator sized and configured to apply adhesive to an engaging surface of the first web.

18. The apparatus of claim 16 wherein said means for securing the segments to the second web further comprises an adhesive applicator sized and configured to apply adhesive to an engaging surface of the second web.

* * * * *